United States Patent [19]

Valbusa et al.

[11] Patent Number: 4,636,457
[45] Date of Patent: Jan. 13, 1987

[54] PROCESS FOR FORMING DIRECT POSITIVE IMAGES, DIRECT POSITIVE SILVER HALIDE ELEMENTS, COMPOSITIONS AND COMPOUNDS AS CHARACTERISTICS FEATURE OF SUCH PROCESSES AND ELEMENTS

[75] Inventors: Luigi Valbusa, Savona; Enzo Coraluppi, Carcare Savona; Andrea Quaglia; Mario Tavella, both of Savona, all of Italy

[73] Assignee: Minnesota Mining and Manufacturing Company, St. Paul, Minn.

[21] Appl. No.: 755,292

[22] Filed: Jul. 15, 1985

[30] Foreign Application Priority Data

Jul. 20, 1984 [IT] Italy .............................. 21991 A/84

[51] Int. Cl.$^4$ .............................................. G03C 5/24
[52] U.S. Cl. ..................................... 430/267; 430/378; 430/375; 430/505; 430/264; 430/406; 430/940; 430/409; 430/410; 430/598; 430/564; 544/198; 544/284; 544/207; 544/324; 544/256
[58] Field of Search ............... 430/598, 564, 409, 410, 430/406, 940, 505, 264, 378, 375, 267; 544/198, 284, 207, 324, 256

[56] References Cited

U.S. PATENT DOCUMENTS 4,115,122  9/1978  Adachi et al. ...................... 430/596
4,278,748  7/1981  Sidhu et al. ........................ 430/410

*Primary Examiner*—Won H. Louie
*Attorney, Agent, or Firm*—Donald M. Sell; James A. Smith; Mark A. Litman

[57] ABSTRACT

Direct positive photographic elements are disclosed employing internal latent image silver halide emulsions associated with developer autoxidation promoter agents constituted by 5 or 6 membered nucleus-containing heterocyclic compounds comprising an azomethine group, whose methine group is substituted with a 5-amino-1,2,4-triazolyl group, and/or copper complex compounds thereof.

Preferably said direct positive photographic elements are multi-layer elements comprising internal latent image type type silver halide emulsion layers sensitized to different regions of the visible light and associated with image-dye providing compounds (photographic color couplers).

18 Claims, No Drawings

PROCESS FOR FORMING DIRECT POSITIVE IMAGES, DIRECT POSITIVE SILVER HALIDE ELEMENTS, COMPOSITIONS AND COMPOUNDS AS CHARACTERISTICS FEATURE OF SUCH PROCESSES AND ELEMENTS

FIELD OF THE INVENTION

The present invention relates to a process for forming a positive image by using a direct positive type silver halide photographic material. More particularly, this invention relates to novel silver halide developer autoxidation promoter agents and to their use in the process wherein a direct positive image is formed by (imagewise) exposure and treatment with a surface developer of an internal latent image silver halide photographic material in the presence of a developer autoxidation promoter agent.

BACKGROUND OF THE ART

It is well-known that a direct positive photographic image can be formed by using a silver halide light sensitive photographic material without any intermediate processing step of treatment or development of any negative photographic image.

The known processes which have been applied to form a positive image by using a positive type silver halide light-sensitive photographic material, excluding special processes, can be mainly classified into the two types.

The first type of process employs a fogged silver halide emulsion and decays the fog specks (latent image) at an exposed area by taking advantage of the solarization or Herschel effect, etc., to form a positive image after development.

Another type of process employs a silver halide emulsion free of fog and carries out a surface development while or after conducting fogging treatment to form a positive image. The fogging treatment may be carried out by conducting whole-surface exposure; using a fogging agent; using an oxidized developer or a developer containing hydrazine or a hydrazine derivative; etc. Usually, the silver halide emulsions employed in the second type of process are of the internal latent image type. After imagewise exposure, the silver halide grains are developed with a surface developer, i.e. one which leaves the latent image sites within the silver halide grains substantially undeveloped. Simultaneously, either by uniform exposure or, preferably, by the use of a nucleating agent, the silver halide grains are subjected to development conditions that would cause fogging of a negative-working photographic element. The internal latent image-forming silver halide grains which received actinic radiations during imagewise exposure develop under such conditions at a comparatively slow rate, as compared to the internal latent image-forming silver halide grains non-imagewise exposed. The result is a direct positive silver image.

In general the latter type of process shows higher sensitivity as compared to the former. However, the latter suffers from poor stability and, when employed in multilayer color light-sensitive materials, variations in maximum density and interference with spectral sensitization, as described for example in U.S. Pat. No. 4,115,122.

SUMMARY OF THE INVENTION

The present invention relates to new compositions and compounds and to their use with photographic elements employing internal latent image silver halide emulsions to get direct positive images. According to the present invention, these emulsions, after imagewise exposure, when developed with a developer with substantially low sulfite content in the presence of a compound and/or composition of the present invention, provide a direct positive image of high maximum density and low minimum density.

Such compositions and/or compounds, which are believed to act as promoter of the aerial autoxidation of the developer, are hereinafter indicated as D.A.P. (Developer Autoxidation Promoter) agents.

They are constituted by heterocyclic compounds with 5 or 6 membered nuclei comprising an azomethine group whose methine group is substituted with a 5-amino-1,2,4-triazolyl group, and/or with copper complexes thereof.

Examples of said D.A.P. agents are a mixture of chemical compounds obtained by heating at high temperature a 3-amino-1,2,4-triazole compound, a chemical compound obtained by heating a 3-amino-1,2,4-triazole compound with a 5,7-diamino-|1,2,4|-triazole-|1,5-a|-|1,3,5|-triazine, and chemical compounds represented by the general formula:

(I)

wherein Q represents $-NR_1R_2$ and $R_1$ and $R_2$ each represent hydrogen or a 5-(1,2,4)-triazolyl group, at least one of them being different from hydrogen; and Z represents the non-metallic atoms necessary to form a 5 or 6-membered heterocyclic nucleus.

Preferably, the photographic elements of the present invention are multilayer color photographic elements, comprising internal latent image silver halide emulsion layers sensitive to different regions of the visible light associated with image dye providing compounds, which, after imagewise exposure, when developed in a p-phenylene diamine color developer composition in the presence of the D.A.P. agents above, provide direct positive color images of good quality.

DETAILED DESCRIPTION OF THE INVENTION

The present invention relates to a mixture of chemical compounds obtained by heating at temperature above 100° C. a 3-amino-1,2,4-triazole compound, said mixture being characterized by the presence of a chemical compound having a molecular weight of about 285. Preferably the mixture is obtained by heating the 3-amino-1,2,4-triazole compound at 170° C. for 5 days, more preferably in the presence of an aprotic solvent, still more preferably in the presence of an o-dichlorobenzene solvent. In another aspect, the present invention relates to a chemical compound obtained by heating at high temperature one mole of a 5,7-diamino-|1,2,4|-triazole-|1,5-a|-|1,3,5|-triazine compound and at least two moles of a 3-amino-1,2,4-triazole compound in an aprotic solvent, said chemical compound having a molecular weight of about 285 and said heating being made preferably at 170° C. for 5 days in o-dichlorobenzene solvent.

In a more general aspect the present invention relates to a 1,2,4-triazolyl-5-amino-azomethine group containing compound (that is an azomethine group in which the hydrogen atom of the methine group is substituted with a 5-amino-1,2,4-triazolyl group), the carbon and the nitrogen atoms of said azomethine group being part of a nitrogen containing heterocyclic nucleus (such as an azole or an azoline compound), and all other heterocyclic nuclei in said compound being preferably comprised of only nitrogen and carbon atoms having five or six ring atoms and no more than three nitrogen atoms within each ring. Said heterocyclic nucleus is preferably triazine, pyrimidine, pyridazine, benzopyrimidine and triazolotriazine.

The compounds of the present invention can be represented by the hereinbefore described formula (I):

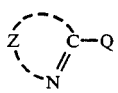
(I)

wherein Q represents —NR$_1$R$_2$ and R$_1$ and R$_2$ each represent hydrogen or a 5-(1,2,4)-triazolyl group, at least one of them being different from hydrogen; and Z represents the non-metallic atoms necessary to form a 5 or 6-membered heterocyclic nucleus.

When such heterocyclic nucleus includes two conjugated 5-(1,2,4)-triazolylamino residues, said chemical compounds can be represented by the following formula:

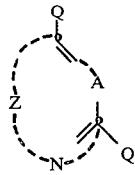
(II)

wherein Q and Z have the same meanings as above and A represents a substituted or non-substituted methine group.

When, particularly, Z represents the non-metallic atoms necessary to form a 6-membered nucleus substituted with at least two Q-groups, as above described, such compounds may be represented by the following formula:

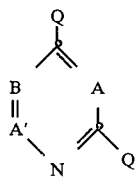
(III)

wherein A has the same meaning as above and A' represents a substituted or a non-substituted methine group and B represents nitrogen or a substituted or non-substituted methine group. Of course when B represents a substituted or non-substituted methine group, Z and A' can represent the non-metallic atoms necessary to form the rest of a 5 or 6-membered fused-on aromatic nucleus as described by the following formula:

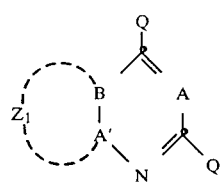
(IV)

wherein Z$_1$ represents the non-metallic atoms necessary to complete a second 5 or 6-membered aromatic nucleus fused on the first nucleus, such as phenyl, or an azoline or an azole group, such as pyridine, diazole or triazole nuclei. Also this fused nucleus may include the above described Q substituents.

Of course both such (simple or fused) azomethine nucleus and the 5-(1,2,4)-triazolyl group of Q-substituent attached thereto can be substituted with various substituents which the skilled in the art may wish to attach to the various positions thereof, such as halogen (for example chlorine, bromine or fluorine), alkyl (preferably having 1 to 6 carbon atoms), alkoxy (preferably having 1 to 4 carbon atoms), phenyl, carboxy, sulfoxy groups directly attached to the nucleus or indirectly attached thereto through an amino, an oxy, an alkylene (preferably low alkylene group), a carbonyl, a sulfonyl group or a group which is a combination of these groups such as carbonylamino, sulfonylamino, oxalkylene, phenyloxyalkylene, phenylcarbonylamino groups. Long (ballasting) alkyl chains may be needed to impart non diffusing properties to the molecule or an improved solubility in oil solvents while COOH and/or SO$_3$H groups may be useful to improve water solubility characteristics.

This invention, particularly, refers to a complex mixture or compound obtained by reacting the mixture of chemical compounds or the chemical compounds above with divalent copper.

In another aspect the present invention relates to an internal latent image silver halide gelatin photographic emulsion having in contact therewith a D.A.P. agent comprising one of the above described compounds (or compound mixtures).

Preferably, the present invention relates to an internal latent image silver halide gelatin photographic emulsion having in contact therewith a D.A.P. agent including a complex of bivalent copper with one of the above described compounds or compound mixtures.

Preferably, the complex of bivalent copper is formed in the presence of a carrier compound dispersed in water or in a water solution of a binder (such as for instance gelatin) to be contacted with said emulsion, in particular a carrier compound selected from the group of a polyethylacrylate, a polyurethane, silica and starch. In a silver halide gelatin photographic emulsion layer, such complex is preferably used in an amount of 0.0001 to 0.1 gram per mole of silver.

In a further aspect, the present invention relates to a direct positive photographic element comprising a support and, coated thereon, at least one gelatin light sensitive silver halide emulsion layer which contains an internal latent image silver halide emulsion reactively associated or in contact with the above D.A.P. agents. Preferably, the direct positive photographic element is a multilayer element comprising at least three gelatin silver halide emulsion layers respectively sensitive to the red, to the green and to the blue region of the visible light, respectively associated with cyan, magenta and yellow dye-forming compounds which contain an internal latent image silver halide emulsion reactively associated or in contact with at least one of the above described compounds (or mixtures) and complexes.

In a further aspect, the present invention relates to a direct positive photographic element having at least one unhardened gelatin layer, a light-sensitive silver halide emulsion layer associated with a colored pigment and a tanning developer, which comprises an internal latent image type silver halide emulsion as described above.

The present invention relates also to a process for forming a direct positive image by developing, after imagewise exposure, an internal latent image type light-sensitive silver halide photographic element with a substantially low sulfite containing developer for silver halide, characterized by the fact of contacting said silver halide emulsion with the D.A.P. agents above during the development step.

Preferably, the invention relates to a process for forming multicolor direct positive images by developing, after imagewise exposure, a multilayer photographic element comprising internal latent image type silver halide emulsion layers, respectively sensitive to the red, to the green and to the blue region of the visible light and associated with image-dye providing compounds, with a p-phenylene diamine color developer composition, which process is characterized by contacting said silver halide emulsions with the D.A.P. agents above during the development step.

Still in particular, the invention relates to a process for forming a direct positive colored relief image by developing, after imagewise exposure, an unhardened gelatin internal latent image type silver halide emulsion photographic element associated with a colored pigment and a tanning developer, with an aqueous alkaline solution, which process is characterized by contacting said silver halide emulsion with the D.A.P. agents above during the development step.

One useful D.A.P. agent according to the present invention is obtained by heating a 3-amino-1,2,4-triazole compound at high temperature, preferably at a temperature above 100° C. and more preferably at a temperature of about 150° C., in particular by heating in the presence of a high boiling aprotic solvent for some days (preferably 5-6 days). A non-melting and poorly soluble (soluble only in alkali solutions and insoluble in water and in the most common organic solvents) mixture of compounds is obtained. By thin layer chromatography, this mixture comprises at least four principal components having Rfs respectively of 0.4, 0.6, 0.8 and 0.9. By mass spectrometry, molecular ions at m/e 151, 178, 193, 218, 260, 285 and 327 have been evidenced and by NMR a triazolyl nucleus including structure has been deducted.

By crystallization with diluted NaOH, the compound having an Rf of 0.6 has been isolated from the mixture with yields of about 30 to 88%. At IR spectrum, this compound showed absorption bands characteristic of triazolyl and triazinyl radicals. At NMR spectrum, it showed three singlets which can be atrributed to three CH triazolyl groups in a ratio of 1:1:1. The molecular weight by acidimetric titration results of about 285.

Another D.A.P. agent of the present invention is obtained by heating one mole of a |1,2,4|-triazole-|1,5-a|-|1,3,5|-triazine compound with an excess over 2 moles of a 3-amino-1,2,4-triazole compound in the presence of a high boiling aprotic solvent as above, at a temperature above 100° C. (preferably above 150° C.) for some days (preferably 5-6 days). By thin layer chromatography, said compound displays an Rf of 0.6, a molecular weight by acidimetric titration of 285 and a structure that NMR and IR spectra suggest to correspond to a 5,7-bis-(1,2,4-triazolylamino)-|1,2,4|-triazole-|1,5-a|-|1,3,5|-triazine compound (as also confirmed by the synthesis method described hereinafter).

Still another useful class of D.A.P. agent are heterocyclic compounds comprising at least one 1,2,4-triazolyl-5-amino-azomethine group, the carbon and nitrogen atoms of said azomethine group being a part of a nitrogen containing heterocyclic nucleus. The preferred D.A.P. agents of this class are those wherein said heterocyclic nucleus is selected within the group including triazine, pyrimidine, pyridazine, benzopyrimidine and triazolotriazine. The D.A.P. agents of this class preferably are represented by the general formulas (I), (II), (III) and (IV) above described. Examples of D.A.P. agents according to the present invention are hereinafter described:

(a) The mixture (1) of compounds obtained by heating 3-amino-1,2,4-triazole.
(b) The compound (2) obtained by heating 3-amino-1,2,4-triazole with 5,7-diamino-|1,2,4|-triazole-|1,5-a|-|1,3,5|-triazine.
(c) The compounds corresponding to the following formulas:

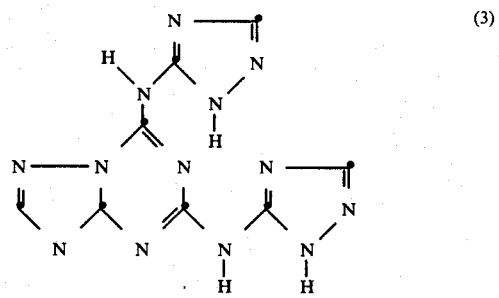

(3)

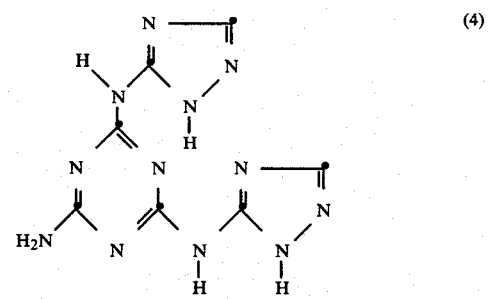

(4)

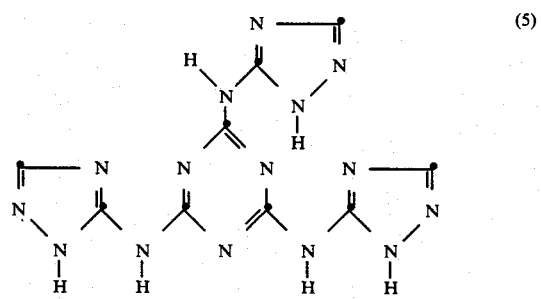

(5)

(6) 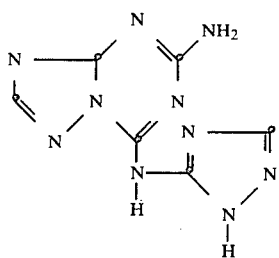

(7) 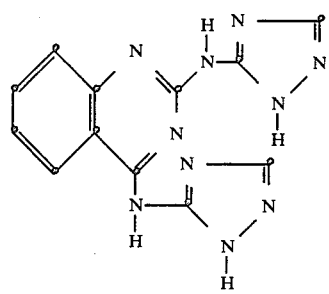

(8) 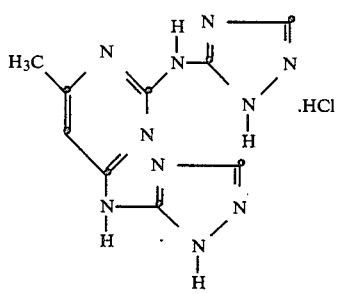

(9) 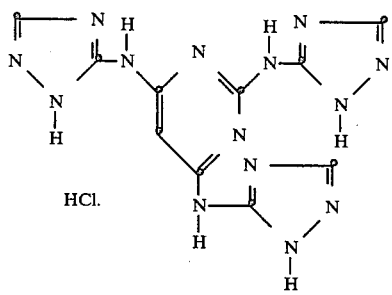

(10) 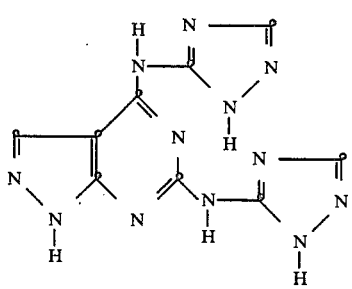

(11) 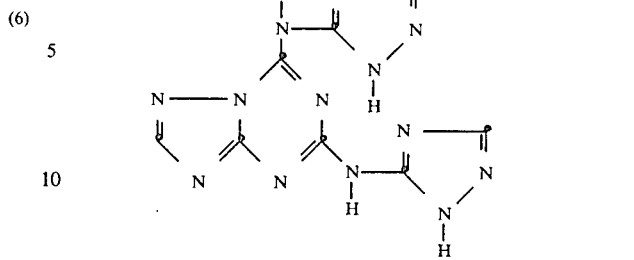

(12) 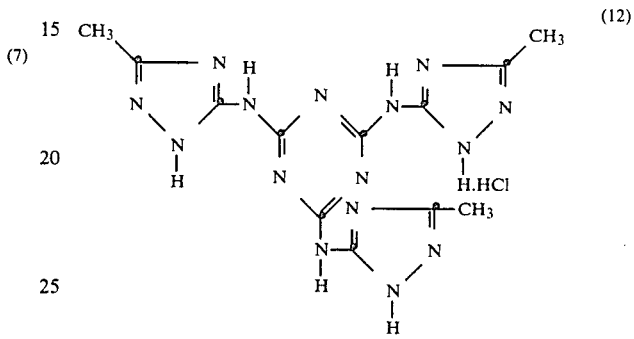

Compound 3 has been prepared by reacting N-(1,2,4-triazolyl)-s-methylisothiourea with 3-guanidino-1,2,4-triazole and it is supposed to have the same structure (equivalent CHN analysis, IR and NMR spectra and RF) of Compound 2. Compound 6 has been prepared by heating N-(1,2,4-triazolyl)-s-methylisothiourea. The other compounds 4 to 5 and 7 to 12 have been prepared by reacting the corresponding chlorinated heterocyclic bases with 3-amino-1,2,4-triazole.

The internal latent image type silver halide emulsions to be used in the present invention are characterized in that when a part of the sample, prepared by applying the emulsion on a transparent support, is exposed for ten seconds under an illumination of 6500 lux from a tungsten lamp and developed for 6 minutes at 20° C. with the surface Developer A reported below (which does not substantially contain a silver halide solvent and which develops the image only on the grain surface), a negative image with a maximum density lower than 0.4 is obtained. If a different part of the same sample of emulsion is exposed in the same way and developed for 6 minutes at 20° C. with an internal developer B, described below (for developing the internal image of the grains), a negative image having a maximum density which is at least 5 times the maximum density obtained with the surface developer A is obtained.

| Surface Developer A | |
|---|---|
| p-Methylaminophenol Sulfate | 2.2 g |
| Hydroquinone | 8.8 g |
| $Na_2SO_3$ | 72.0 g |
| $Na_2CO_3$ | 48.0 g |
| KBr | 4.0 g |
| Water to make | 1 liter |
| Internal Developer B | |
| Surface developer A | 1 liter |
| $Na_2S_2O_3$ | 10 g |

The silver halide included in said emulsions may be for example silver bromide, silver chloride, silver chlorobromide, silver iodobromide, silver chloroiodobromide, etc.

The internal latent image type silver halide emulsions according to this invention may include those emulsions which are prepared by various processes described in the art. There may be mentioned for instance a conversion type silver halide emulsions described in U.S. Pat. Nos. 2,590,250; 3,260,650; 3,703,584; in British patent 1,450,474 and in Japanese patent 65,799/66; a layered grain structure type silver halide emulsions as described in U.S. Pat. Nos. 3,957,488; 3,206,313; the core-shell type silver halide emulsions as described in U.S. Pat. Nos. 3,317,322; 3,717,466 and 3,367,778; in British Pat. Nos. 1,027,149; 1,306,801; 1,385,039; in Belgian Pat. Nos. 721,812 and 722,149 and in French Pat. No. 2,178,982.

The silver halide emulsions used according to this invention may contain the usual emulsion additives, provided that the surface sensitivity is kept as low as possible. The emulsion may also be spectrally sensitized. As spectral sensitizers, which may be used in this invention, there may be mentioned the usual monomethine or polymethine dyes such as cyanines, merocyanines, trinuclear or higher nuclear cyanines, trinuclear or higher nuclear merocyanines, hemioxonoles, oxonoles, hemicyanines and streptocynaines. Among the nitrogen-containing nuclei constituting them, there can be usefully mentioned thiazoline, thiazole, rhodanine, thiohydantoin, oxazolidinedione, barbituric acid, thiobarbituric acid and pyrazolone. Such nuclei may be substituted with alkyl, hydroxyalkyl, sulfoalkyl, carboxyalkyl, halogen, phenyl, cyano or alkoxy and may optionally be condensed with a carbon ring or a heterocyclic ring.

Sensitizers of this type have been for instance described by F. M. Hamer, *The Cyanines And Related Compounds*, 1964, Interscience Publishers, John Wiley and Sons.

The silver halide according to this invention may be super-sensitized. The super-sensitization process is described, for example, in Review of Super-Sensitization, Phot. Sci. Eng., vol 18, no. 4, 418 (1974).

A simple exposure and development process can be used to form a direct-positive image according to the present invention. In one embodiment, a photographic element comprising at least one layer of a silver halide emulsion as described above and associated with the D.A.P. compositions and compounds as described above can be imagewise exposed to light and then developed in a substantially low sulfite content silver halide surface developer (as hereinafter defined).

The expressions "associated" or "reactively associated" mean that the silver halide emulsions and the D.A.P. agents are so arranged in relation to each other than an interaction between them can take place to produce the development of silver halide grains which have not been imagewise exposed as compared to imagewise exposed silver halide grains. A way to obtain said association is that of contacting said D.A.P. agents with the emulsion prior to or during development. Said D.A.P. agents can be contained in a layer of silver halide emulsion, a layer adjacent thereto, a developing solution or a bath for treatment prior to development or in an activator solution.

The D.A.P. agents above can be employed in any desired concentration that allows the selective development of the (imagewise) unexposed silver halide grains, as compared to the same exposed silver halide grains.

In a preferred form the D.A.P. agents are incorporated into the silver halide emulsion in concentrations ranging from 0.0001 to 0.1 grams per mole of silver halide. In the developing solution or in the treatment or activator solutions, their amount is preferably from 0.01 to 0.1 mg per liter of solution.

It is clear that the term "surface developer" encompasses those developers which reveal the latent image located on the surface of a silver halide grain, but do not reveal the internal latent image located at their inside. The term "substantially low sulfite content" encompasses those developers which have a molar ratio sulfite/developing agent lower than 5 and preferably lower than 3. The substantially low sulfite content silver halide surface developers can generally utilize any of the silver halide developing agents or reducing agents. However the developing bath or composition are generally free of a silver halide solvent (such as water-soluble thiocyanates, water-soluble thioethers, thiosulfates and ammonia) which would disrupt or dissolve the (exposed) grain to reveal the internal image thereof. Typical silver halide developing agents in developing compositions include hydroquinones, catechols, aminophenols, 3-pyrazolidones, ascorbic acid and its derivatives, reductones and color developing agents, that is primary aromatic amine developing agents, such as aminophenols and para-phenylene diamines.

In a specific embodiment, the photographic elements according to the present invention are intended to produce multicolor images. Said elements contains at least three superimposed color-forming layer units coated on a support. Each of the layer units is comprised of at least one silver halide emulsion layer. At least one of the silver halide emulsion layers, preferably at least one of the silver halide emulsion layers in each color forming layer unit and most preferably each of the silver halide emulsion layers contain an emulsion associated to a D.A.P. agent of this invention as described above. The emulsion layers of one of the layer units are primarily responsive to the blue region of the spectrum, the emulsion layers of a second of the layer units are primarily responsive to the green region of the spectrum and the emulsion layers of a third of the layer units are primarily responsive to the red region of the spectrum. The layer units can be coated in any conventional order. In a preferred layer arrangement, the red-responsive layer unit is coated nearest the support and is overcoated by the green-responsive layer unit, a yellow filter layer and a blue-responsive layer unit. The layer units are each associated with at least one image-dye forming compound. (By "associated" is meant that the silver halide emulsion and the dye-forming compounds are so arranged in relation to each other than an interaction between them can take place to produce an imagewise correspondance between the silver image formed and the dye image. The associated image-dye forming compounds may be incorporated in the silver halide emulsion layer or less preferably in a layer adjacent thereto or, but still less preferably, in a development or activator bath).

Incorporated dye-forming couplers constitute exemplary preferred image-dye providing compounds. The blue, green and red-responsive layer units preferably contain yellow, magenta and cyan image-dye providing couplers, respectively.

Preferred couplers used in the green sensitive emulsion layer, which form magenta dyes upon reaction with oxidized color developing agents, are pyrazolone couplers, pyrazolotriazole couplers, pyrazolobenzimidazole couplers, cyanoacetylcumarone couplers, and indazolone couplers. Representative couplers are described in such patents and publications as U.S. Pat. Nos. 2,600,788; 2,369,489; 2,343,703; 2,311,082; 2,673,801; 3,152,896; 3,519,429; 3,061,432; 3,062,653; 3,752,067; 2,908,573 and in "Farbkuppler—eine Literaturübersicht", published in Agfa-Mitteilungen, Band II, pp. 126 to 156, (1961).

Preferred couplers used in the blue-sensitive emulsion layer, which form yellow dyes upon reaction with oxidized color developing agents, are acylacetanilides such as benzoylacetanilides and pivalylacetanilides. Representative couplers are described in the following patents and publications: U.S. Pat. Nos. 2,875,057; 2,407,210; 3,265,506; 2,298,443; 3,048,194; 3,447,928 and in "Farbkuppler—eine Literaturübersicht" above at pages 112 to 126.

Preferred couplers used in the red-sensitive emulsion layer, which form cyan dyes upon reaction with oxidized color developing agents, are phenols and naphthols. Representative couplers are described in the following patents and publications: U.S. Pat. Nos. 2,772,162; 2,895,826; 3,002,836; 3,034,892; 2,474,293; 2,423,730; 2,367,531; 3,041,236 and in "Farbkuppler—eine Literaturübersicht" above at pages 156 to 175.

In order to render the couplers non-diffusible, a group having an hydrophobic residue with about 8 to 32 carbon atoms is introduced into the coupler molecule. Such residue is called "ballast group". The ballast group is linked to the coupler nucleus directly or through an imino, ether, carbonamido, sulfonamido, ureido, ester, imido, carbamoyl, sulfamoyl, etc. bond. Examples of ballast group are specifically illustrated in U.S. Pat. No. 4,009,038.

Usefully, said dye forming couplers can be included into the silver halide emulsion layers by various methods known in the photographic art. Couplers having a water-soluble group, such as a carboxyl group, a hydroxy group, a sulfonic group or a sulfonamido group, can be added to the emulsion according to the Fisher process, i.e. by dissolving them in an alkaline water solution. Hydrophobic couplers and other additives can be added to the silver halide emulsion according to the so-called "dispersion technique", as for example described in U.S. Pat. Nos. 2,322,027; 2,304,939; 2,801,170; 2,801,171 and 2,991,177. It substantially consists of dissolving the compounds (to be added) in an organic solvent which is substantially water-immiscible and has a high boiling point (for instance higher than 200° C.), preferably with the aid of a partially water miscible solvent having a lower boiling point (for instance between 20° and 170° C.) and then of dispersing the so-obtained solution in an aqueous substance, in the presence of a dispersing agent in the form of small droplets (of sizes ranging from 0.1 to 1μ, more preferably from 0.15 to 0.30μ).

Examples of substantially water-immiscible organic high-boiling solvents are dibutylphthalate, tricresylphosphate, triphenylphosphate, di-n-hexyladipate, dimethylsebacate, quinitol-di-(2-ethylesoate) and 1,4-cyclohexyldimethylidene-di-(2-ethylesoate) used alone or in combination.

Examples of low-boiling partially water miscible organic solvents are methylacetate, ethylacetate, propylacetate, butylacetate, butylpropionate, cyclohexanol, nitromethane, chloroform, cyclohexane, ethyl alcohol, acetonitrile, dimethylformamide, dioxane, acetone, methylethylketone used alone or in combination.

Of course, it is possible to add some couplers according to the Fisher process and other couplers according to the dispersion technique.

Such magenta, yellow and cyan dye-forming couplers may be used in combination with DIR compounds, that are compounds which during development release a development inhibiting compound. Compounds of this type are for instance the DIR couplers which release a development inhibiting compound during the reaction with the oxidation product of a color developer to form a dye, such as those described e.g. in U.S. Pat. Nos. 3,227,554; the TIMING-DIR couplers which release a development inhibiting compound with the capability of controlling the release time, such as those described e.g. in GB patent application Nos. 2,010,818 and 2,072,363; DIR hydroquinones which release a development inhibiting compound upon oxidation-reduction exchange with the oxidation products of the color developing agent, such as those described in U.S. Pat. No. 3,639,417 and 3,379,529; other DIR substances which release development inhibiting compounds during the reaction with the oxidation product of a color developing agent to form a substantially colorless compound, such as those described in U.S. Pat. No. 3,958,993; 3,961,959; 3,938,996; 3,928,041 and 3,632,345.

Such DIR compounds are made non diffusible by means of ballasting groups (as described above for the couplers) and included into the silver halide emulsion layers of the photographic element according to the various methods described above.

The silver halide emulsions used in the red-sensitive, green-sensitive and yellow-sensitive layers of the present invention are preferably a fine dispersion of silver chloride, silver bromide, silver chloro-bromide, silver iodo-bromide, silver chloro-iodo-bromide in a hydrophilic polymer. As a hydrophilic polymer, the conventional polymers used in the photographic art can be advantageously used. They include gelatin, a gelatin derivative such as acylated gelatin, graft gelatin, etc., albumin, arabic gum, agar agar, a cellulose derivative such as hydroxyethylcellulose, carboxymethylcellulose, etc., a synthetic resin such as polyvinyl alcohol, polyvinylpyrrolidone, polyacrylamide, etc. The silver halide can have uniform grain sizes or a broader distribution of the grain sizes. Furthermore, the silver halide grain sizes range from about $0.1\mu$ to about $3\mu$. The silver halide emulsion can be prepared by following a single-jet, double-jet method or a combination of such methods or can be ripened using for instance an ammonia, a neutralization or an acid method, etc.

The silver halide emulsion used as the light-sensitive emulsion layer in this invention preferably is not surface chemically sensitized. When the internal image type silver halide emulsion is a core-shell type, the core can be chemically sensitized, such as, for instance, by a gold sensitization method as described in U.S. Pat. Nos. 2,399,083; 3,597,856 and 2,597,915; a reduction sensitization method as described in U.S. Pat. Nos. 2,487,850 and 2,521,925; a sulfur sensitization method as described in U.S. Pat. Nos. 1,623,499 and 2,410,689; a sensitization method using metal ions other than silver as described in U.S. Pat. Nos. 2,566,263; 2,566,245 and 2,566,263; or a combination of these methods.

The silver halide emulsion used in this invention can further contain stabilizers such as a 4-hydroxy-1,3,3a,7- tetrazaindene derivative, etc., antifoggants such as a mercapto compound and a benzotriazole derivative, coating aids, hardening agents, wetting agents, sensitizers such as an onium derivative, for instance a quaternary ammonium salt as described in U.S. Pat. Nos. 2,271,623 and 2,288,226 and also a polyalkylene oxide derivative as described in U.S. Pat. Nos. 2,708,162; 2,531,832; 2,533,990; 3,210,191 and 3,158,484. The silver halide emulsion layer further can contain an irradiation preventing dye.

Furthermore, the color photographic material of this invention can contain layers such as a filter layer, a mordant dye-containing layer, a colored layer containing dispersed a hydrophobic dye (for antihalo or color correction purposes), intermediate layers.

The silver halide emulsion used in this invention can be coated on various supports such as, for instance, a cellulose acetate film, a polyethylene terephthalate film, a polyethylene film, a polypropylene film, a glass plate, a baryta-coated paper, a resin-coated paper or a synthetic paper.

According to the present invention, the D.A.P. agents above are believed to promote the self-oxidation of the color developer agent only in the unexposed areas. The oxidized color developer agent, which is a substituted p-phenylene diamine compound, reacts with the color couplers associated to the silver halide emulsion layers to give a direct positive color image.

The color developer agents especially useful in the present invention include p-phenylene diamine and N,N-dialkyl-p-phenylene diamine compounds, wherein the alkyl groups or the aromatic nucleus may be substituted, for example: N,N-diethyl-p-phenylene diamine hydrochloride, 2-amino-5-diethylaminotoluene monohydrochloride, 4-amino-N-ethyl-N-|β-methanesulfonamidoethyl|-m-toluidine sesquisulfate monohydrate, 4-amino-3-methyl-N-ethyl-N-|β-hydroxyethyl|-aniline sulfate, 4-amino-3-(β-methylsulfonamidoethyl)-N,N-diethylaniline hydrochloride, 4-amino-N,N-diethyl-3-(N'-methyl-β-methylsulfonamido)-aniline hydrochloride and similar color developing agents disclosed in U.S. Pat. Nos. 2,552,241 and 2,566,271, 4-amino-3-methyl-N-ethyl-N-(β-methansulfonamidoethyl)-aniline sesquisulfate monohydrate disclosed in U.S. Pat. Nos. 3,875,227, p-amino-Nethyl-β-hydroxyethyl-m-toluidine mononitrate and dinitrate disclosed in U.S. Pat. No. 3,297,760 and 4-amino-N-(β-alkoxyalkyl)-N-alkyl-3-alkyl-aniline di-p-toluensulfonic acid salts disclosed in U.S. Pat. No. 3,656,950.

Other useful p-phenylene diamine developing agents are disclosed in J.A.C.S., 73, 3100-3125 (1951).

The color developing agents above are used in color developing compositions over a wide range of concentrations, with an operable range of from about 0.5 g/l to about 15 g/l and a preferred range of from 1.0 g/l to about 10.0 g/l. Other addenda used to advantage in these developing compositions include benzyl alcohol, alkali metal chlorides, alkali metal bromides, alkali metal sulfites, alkali metal salts of weak acids (e.g. carbonates, borates, phosphates, etc.) and any other salts capable of buffering in the range of from about 9 to about 13, stabilizers for color developing agents (e.g. hydroxylaminesulfate, dihydroxyacetone, glycolaldehyde, etc.), water softeners (e.g. sodium hexametaphosphate, etc.). A typical color developing composition used in the present invention is as follows:

| | |
|---|---|
| Benzyl alcohol | 0-15.0 ml/l |
| Alkali metal chloride (e.g. NaCl and KCl) | 0.1-15.0 g/l |
| Alkali metal bromide (e.g. NaBr and KBr) | 0.1-1.0 g/l |
| Stabilizing agent (e.g. hydroxylamine sulfate) | 0.1-5.0 g/l |
| Alkalimetal sulfite (e.g. $Na_2SO_3$ and $K_2SO_3$) | 0.1-5.0 g/l |
| Color developing agent | 1.0-10.0 g/l |
| Buffering agent | 10.0-50.0 g/l |
| pH | 9.0-13.0 |

The photographic element is contacted with the developer solution at a temperature normally in the range of from about 15° C. to about 40° C. The optimum developing times depends upon the particular elements, the particular development solution, temperature and other factors and is easily determined by methods well-known in the art. Treatment with the aqueous developer composition is advantageously accomplished by any of the methods conventionally used including immersion of the element in a tank of developer, contacting and coating the element with a film of developer transferred to the element with any appropriate means, such as roller applicator, coating hopper, etc. After color development, the color developed element is processed in a bleaching bath and fixing bath or, alternatively, in a bleach-fixing bath. The element is advantageously given a stabilizing process prior to drying. In one process sequence for doing this, the color developed element is treated with the following steps: a stop-fix, wash, bleach, wash, fix, wash and stabilize. In another process sequence, the color developed element is bleach-fix, washed and stabilized as described in U.S. Pat. No. 3,189,452.

According to an embodiment, the photographic element according to the present invention are intended to produce color relief images by the method of tanning development. The method of tanning development, known for instance from U.S. Pat. No. 3,364,024, briefly consists of imagewise exposing a substantially unhardened gelatin silver halide emulsion and developing it with a developing agent whose oxidation product is capable of hardening the gelatin. Gelatin is therefore imagewise hardened in the development regions and washed away in the non-development regions under formation of a relief image. If the gelatin layer containing dispersed the emulsion or, preferably, a gelatin layer adjacent thereto contains a pigment, the developed and hardened regions will appear colored by said pigment, while the undeveloped regions, whose gelatin has been washed away, will appear colorless (or of the support color). Image is therefore formed by developed silver (which, being used in small quantities, gives a low contribution to the image density) and by the pigment which intensifies the density of the obtained image. Normally, the tanning developer is contained in the emulsion layer or in a layer adjacent thereto, the developing process being activated by an alkali bath. Of course, when an internal latent image emulsion associated to a D.A.P. agent of the present invention is used in a tanning development photographic element, the unexposed areas are hardened, while the exposed areas are not and can be washed away thus giving rise to a relief direct positive image. The preferred binding agent for the silver halide layer and the pigment containing layer and for the layer containing both the silver halide and the pigment is gelatin. However, other binding agents which can be hardened by the oxidized developer can be used, such as polyvinyl alcohol and polyacrylamide. The preferred developing agent is hydroquinone but other tanning developer agents such as catechol, pyrogallol, metol, amidol or paraminophenol may be used. The developing agent may be included in the silver halide emulsion layer and/or in the pigment containing layer (in this case, development can be obtained by using an alkaline activator) or in a low sulfite containing alkaline developing bath. Preferably, the developing agent is introduced into the silver halide emulsion layer and/or in the pigment containing layer to avoid stability defects of the developing bath in the absence or low presence of sulfite. Any dye or pigment used in photography which is diffusable in the gelatin layer even when in aqueous solution, and which is not reactive with the photographic emulsion to give negative phenomena such as fogging and desensitization, can be used in the materials for tanning development provided it is introduced by methods and with surface active agents which are compatible with the gelatin and with the silver halide emulsion used and compatible with the method for obtaining a colored relief image. As regards this, the use of carbon as a pigment did not provide highly desirable because it showed a certain tendency to harden gelatin even in non-development regions. The replacement of carbon with organic pigments, allowed photographic elements to be obtained with increased stability during time. A particularly useful tanning development photographic element to be used with an internal latent image silver halide emulsion associated with the D.A.P. agents of the present invention, is described in U.S. Pat. No. 4,369,245, the improvement thereof consisting of reducing the silver content in the silver halide emulsion layer in terms both of absolute value and of its proportion with respect to the quantity of gelatin present in the layer(s).

The presence of copper ions during the development step is believed to be useful to the purposes of the present invention. A few micromoles of copper, in particular from 2 to 50 micromoles of copper ions, are believed to be sufficient to create an effective amount of the complex. To the purposes of the present invention it is preferred to use a complex between copper ions and the chemical compounds of the present invention either prepared inside the photographic element or, preferably, preformed outside the photographic element and subsequently added to the photographic element. It has been particularly found, as already indicated, that a better consistency of photographic results can be obtained by forming (either before, during or after their introduction into the photographic elements) the complex of bivalent copper and the D.A.P. agents of the present invention in the presence of a dispersion of fine particles of a substantially inert (from a strict chemical photographic point of view) compound (carrier) insoluble in water and in aqueous gelatin solutions or an aqueous solution of a compound soluble in water but incompatible with the dry gelatin of the photographic element. Examples of aqueous dispersions of compounds insoluble in water and in aqueous gelatin solutions are vinyl addition polymer latices, which are obtained upon emulsion polymerization of suitable monomers known in the art: the acrylic and methacrylic acid ester type monomers, suc as ethylacrylate, methylmethacrylate, methylacrylate, etc.; alkyl-substituted acrylamide, such as N,N-dibutylacrylamide, N-ethylacrylamide, etc., diene monomers, such as butadiene, isoprene, dimethylbutadiene, chloroprene, etc.; aromatic monomer compounds such as styrene, vinyltoluene, etc.; acrylonitrile, methacrylonitrile, vinylpyridine, vinylquinoline and other commonly known similar monomers. Such polymers may be usefully dispersed in water or aqueous solutions in the form of very small particles having dimensions ranging from 0.03 ro 0.4 microns, more preferably from 0.04 to 0.1 microns. Methods for preparing such water dispersions are described in the European patent application Ser. No. 48,700. Preferred polymers for the purposes of the present invention are the acrylic acid ester polymers chosen within the class of polyethylacrylate, polybutylacrylate, polyethoxyethylacrylate, polyhexylacrylate and polyethylhexylacrylate, the most preferred being polyethylacrylate. Other examples of aqueous dispersions of compounds insoluble in water and in aqueous gelatin solutions are polyurethane polymer latices, which are obtained from a polyol component and an isocyanate component. Polyurethane latices are well-known in the art as described, for example, in U.S. Pat. Nos. 2,968,575; 3,213,049; 3,294,724; 3,565,844; 3,388,087; 3,479,310 and 3,873,484. Methods for preparing polyurethane latices and examples of polyurethane latices, useful to the present invention, are described in the European patent application Ser. No. 14,921. Still other examples of aqueous dispersions of compounds insoluble in water and in aqueous gelatin compositions are colloidal silicas, in particular silicas having an average particle size of 7 m$\mu$ to 120 m$\mu$. Such colloidal silicas contain silicon dioxide as a major component (e.g. in an amount of about 98% by weight or more of the total solids present) and allumina or sodium alluminate as a minor component (e.g. in an amount of about 2% by weight or less of the total solids present). Further, the colloidal silica may contain (e.g. in an amount of about 0.05 to 2.0% by weight based on the $SiO_2$), as a stabilizer, an inorganic base such as sodium hydroxide, potassium hydroxide, lithium hydroxide or ammonium hydroxide or an organic salt such as a tetramethylammonium salt, etc. Particularly, potassium hydroxide or ammonium hydroxide is preferred as the stabilizer for colloidal silica. Colloidal silica is described in detail for example in *Surface And Colloidal Science,* vol. 6, pages 3–100, edited by Egon Matijevi , John Wiley and Sons (1973). Examples of the colloidal silicas which can be used include those commercially available under the name: Ludor AM, Ludox AS, Ludox LS, Ludox TM and Ludox MS by E. I. DuPont de Nemours and Co. (USA); those commercially available under the name Snowtex Ao, Snowtex C, Snowtex N and Snowtex O by Nissan Chemicals Ind. Ltd.; those commercially available under the name: Syton C-30 and Syton 200 by Mousants Co. (USA) and those commercially available under the name: Nalcoag 1030, Nalcoag 1060 and Nalcoag 1D-21-64 by Nalco Chem. Co. (USA). Examples of compounds soluble in water, compatible with aqueous gelatin solutions (i.e. not showing phase separation in aqueous solution with the gelatin), but incompatible with the dry gelatin of the layer are polyvinyl alcohols, which are prepared by saponifying polyvinyl acetates and are water-soluble when at least 80% of the acetyl groups are saponified. Particularly useful for the purpose of the present invention are polyvinyl alcohols with at least 88% and preferably at least 98% of the acetyl groups are saponified and have a viscosity at 20° C. in a 4% aqueous solution between 5 and 40 cP and preferably between 5 and 20 cP, a viscosity higher than 40 cP being less preferred since it would cause defect and excessive turbidity in the layer. Other examples of compounds soluble in water, compatible with aqueous gelatin solutions and incompatible with the dry gelatin of the layer are dextranes, which are polysaccharides having an empirical formula which include $C_6H_{10}O_5$ monomer units connected to form glucoside bonds. The preferred dextranes according to the present invention have an average molecular weight of about 500,000 and a relative viscosity of 5 cP at 23° C. when in a 20% mixture with water, dextranes with molecular weights lower or higher than the above reported value (e.g. 100,000 through 900,000) being also useful for the purpose of the present invention, provided that the aforesaid water solubility and gelatin incompatibility requirements be satisfied. Still other examples of compounds incompatible with dry gelatin are the starches and the water-soluble starches, which are obtained by heating or treating starches with acids or alkalis, as known in the art (polysaccharides formed by linear chains of glucoside units linked in 1,4 position as α-glucoside having a molecular weight from about 90,000 to 350,000, linked laterally with lateral chains in the 1,6 position, which lead to macromolecular compounds, having molecular weights of about 4,000,000 to 6,000,000). The preferred process for preparing the complex copper ions-chemical compounds of the present invention onto a compound selected within the class of vinyl addition polymer latices, polyurethane polymer latices, colloidal silicas, polyvinyl alcohols, dextranes and starches is the following: a water solution of soluble bivalent copper salt of organic or inorganic acid (such as acetic, hydrobromic, hydrochloric, chloric, citric, formic, glucosic, glycinic, nitric, salicyclic, sulfuric and tartaric acids) and a water solution in alkaline hydroxides of a chemical compound of the present solution are added to an aqueous dispersion or solution of the selected compounds above. Generally it is preferred to add very diluted solutions (such as between 0.001 and 0.1% by weight) of the bivalent copper and the chemical compounds of the present invention (such as, for example, concentrations from about 0.001 to about 0.1% by weight) to concentrated dispersions or solutions of the selected compounds above (such as, for example, between 11 to 30% by weight). This allows a better dosage of the low amounts of the complex necessary to obtain the desired results, to be added to the silver halide emulsion according to the present invention. In the process above, it is preferred to add a relatively larger amount of copper ions with respect to the amount of the chemical compounds, the weight ratio between copper ions and chemical compounds being preferably 2:1 and more preferably 10:1.

In a preferred aspect, the internal latent image silver halide emulsion, used to the purposes of the present invention, is associated with a 2-thiobarbituric acid compound (such as 2-thiobarbituric acid, 5,5-diethyl-2-thiobarbituric acid, 5-benzal-2-thiobarbituric acid, 6-imino-2-thiobarbituric acid, 1-ethyl-5-benzal-6-imino-2-thiobarbituric acid). The developability of the photographic element of the present invention, in fact, can be improved with various means known to the skilled in the art, but particularly has been found to be improved by the presence of the thiobarbituric acid derivatives, especially in color photographic elements of the present invention in which the presence of spectral sensitizers and the multilayer structure decrease the maximum density of the developed element. Such 2-thiobarbituric acids may be preferably incorporated directly into the light sensitive silver halide emulsion of the present invention and useful amounts of 2-thiobarbituric acids are in the range from $10^{-5}$ to $10^{-2}$ moles of each silver mole.

In a preferred embodiment, the internal latent image silver halide emulsion, used to the purposes of the present invention, is associated with a diffusion resistant hydroquinone, especially when it is incorporated in multicolor photographic coupler-containing elements comprising three layer units respectively forming magenta, cyan and yellow color as described above. The diffusion resistant hydroquinones preferred to the purposes of the present invention include the nucleus-substituted hydroquinones represented by the following general formula:

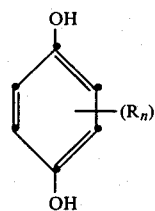

wherein R is an alkyl group, an alkoxy group, an arylalkyl group, an aryloxy group, an arylalkoxy group, a carbamoyl group, a sulfamoyl group, an acyl group, an alkoxycarbonyl group or an aryloxycarbonyl group, preferably including alkyl groups having 1 to 16 carbon atoms; and n is a positive number from 1 to 4. The above said carbon atoms chains can be furthermore substituted with a substituent such as a halogen atom, an alkyl group, an aryl group, an alkoxy group, an aryloxy group, a carboxyl group, an alkoxycarboxyl group, an aryloxycarbonyl group, an aryloxy group, a carbamyl group, a sulfamyl group, an acylamino group, an imido group or a hydroxyl group. Specific examples of nucleus substituted hydroquinones are described for instance in U.S. Pat. Nos. 2,336,327; 2,360,290; 2,384,658; 2,403,721; 2,418,613; 2,675,314; 2,701,197; 2,704,713; 2,710,801; 2,722,556; 2,728,659; 2,732,300; 2,735,765; 2,816,028; 3,062,884; 3,236,893; in GB patents 557,750 and 557,802; in German patent application Ser. No. 2,149,789, as well as in Journal of Organic Chemistry, vol. 22, pages 772 to 774. Typical diffusion-resistant hydroquinone compounds corresponding to the above formula which are included in this invention are, for example, 2-(n)-octyl-5-methyl-hydroquinone, 2-(n)-dodecyl-5-methylhydroquinone, 2,5-di-(n)-octyl-hydroquinone, 2,6-di-(n)-dodecylhydroquinone, 2,5-di-(t)-butylhydroquinone, 2,5-di-(t)-octylhydroquinone and 2,5-di-(t)-hexadecylhydroquinone. The diffusion-resistant hydroquinones are introduced into the gelatin layer of the photographic element of the present invention in ways known from the photographic art. A typical method of addition is the dispersion technique already described which gives the possibility of incorporating them, when used, together with the couplers. In fact, the developability of the multilayer color photographic element according to the present invention is to be improved by the presence of non-diffusing hydroquinones and the maximum density of the element upon development is higher in the presence of said compounds.

The following examples illustrate the preparations of the D.A.P. agents and of the photographic elements according to the present invention.

The following couplers were used in association with light-sensitive (possibly sensitized with optical sensitizers) photographic emulsions:

Coupler A: α-pivalyl-α-(3-dichloro-1,2,4-triazolyl)-5-[γ-(2,4-ditert.amylphenoxy)-butyramido]-2-chloroacetanilide (Coupler no. 6 of U.S. Pat. No. 4,182,630).

Coupler B: 1-(2',4',6'-trichlorophenyl)-3-[3''-(2''',4'''-ditert.amylphenoxy-acetamido)-benzamido]-5-pyrazolone (Coupler no. 7 of U.S. Pat. No. 2,600,788).

Coupler C: 1-(2'-methoxy-4',6'-dichloro)-phenyl-3-p-dodecylphenylureido-5-pyrazolone (Coupler no. 3 of U.S. Pat. No. 3,841,794).

Coupler D: 1-hydroxy-2-[δ-(2',4'-ditert.amylphenoxy)-n-butyl]-naphthamide (Coupler no. 1 of U.S. Pat. No. 2,474,293).

Coupler E: 2-α-(2',4'-ditert.amylphenoxy)-n-butyrylamino-4,6-dichloro-5-methylphenol (Coupler no. 19 of U.S. Pat. No. 3,790,379).

Coupler F: 2-(2',4'-ditert.amylphenoxy)-acetamido-4,6-dichloro-5-methyl-phenol (Coupler no. 1 of U.S. Pat. No. 4,009,038).

The following developer solutions were used in the development processes for the photographic elements of the following examples.

| Black and White Developer A | |
|---|---|
| p-Methylaminophenol Sulfate | 2.2 g |
| Hydroquinone | 8.8 g |
| $Na_2SO_3$ | 72.0 g |
| $Na_2CO_3$ | 48.0 g |
| KBr | 4.0 g |
| Water to make | 1 liter |
| Black and White Developer B | |
| Black and White Developer A | 1 liter |
| $Na_2S_2O_3.5H_2O$ | 10.0 g |
| Water to make | 1 liter |
| Color Developer C | |
| Sodium hexametaphosphate | 2 g |
| $Na_2SO_3$ | 4 g |
| CD2 | 3 g |
| $Na_2CO_3$ | 17 g |
| KBr | 2 g |
| $H_2SO_4$ for pH | 10.65 |
| Water to make | 1 l |
| Color Developer D | |
| Benzyl alcohol | 14.5 ml |
| $NH_2OH.HCl$ | 2.2 g |
| $K_2S_2O_5$ | 1.6 g |
| CD3 | 5.6 g |
| KOH (35% w/w) | 7.0 ml |
| DTPA | 2.5 g |
| $K_2CO_3$ | 26 g |
| KBr | 0.6 g |
| Water to make | 1 l |

EXAMPLE 1

Preparation of Composition no. 1

150 g of 3-amino-1,2,4-triazole were put into a three-necked flask equipped with a mechanical stirrer, a thermometer and a reflux condenser. The compound was melted and heated at 170° C. under stirring for 5–6 days. During this time there was formation of ammonia and later a solid phase was formed in the liquid phase. The mass was cooled and the unreacted aminotriazole was washed off with water. The remaining solid phase was filtered and washed with water. At the end of filtration the solid phase was dispersed in water and boiled for one hour. The suspension was hot filtered and washed with ethanol. The product was dried at 110° C. thus obtaining few grams of a non-melting mixture of compounds soluble in sodium hydroxide solution and concentrated hydrochloric acid, insoluble in water and the most common organic solvents. For acidification of the alkaline solution a gelatinous precipitate was formed. 50 mg of the compound were dissolved in 0.25 ml of ethylenediamine and 1 ml of dimethylformamide. A drop of such solution was chromatographed on a thin layer of silica gel, eluted with a solution of 20 ml of ethylene diamine and 80 ml of dimethylformamide for 90 minutes. Under irradiation with UV light of about 254 nm four principal spots having Rfs of 0.4, 0.6, 0.8 and 0.95 were evidenced. The mass spectrometry analysis evidenced a mixture of at least seven compounds with the following molecular weights: 151, 218, 285; 126, 193, 260 and 327.

From the solution of the mixture in sodium hydroxide, a compound crystallized out by cooling, with a yield of 80%. After treatment with diluted hydrochloric acid, a compound having a single spot at Rf 0.6 was obtained, whose NMR spectrum presents three singlets which can be attributed to 3 triazolyl CH groups with a ratio of 1:1:1.

EXAMPLE 2

Preparation of the Compound 2

A 1 liter three-necked flask provided with a stirrer, reflux condenser, thermometer and an external oil bath was filled with 30.2 g of diamino-triazine-triazole (prepared according to Haiser et al., J. Org. Chem., 18, 1610), 44 g of 3-amino-1,2,4-triazole and 500 ml of o-dichloro-benzole. Stirring was begun and the temperature was raised to 170°–175° C. by heating externally. Such a temperature was kept for 5 days and the solution, thus obtained, was then cooled at room temperature and filtered. The obtained mass was hot ground three times in 500 ml of demineralized water, filtered and dried at constant weight. 57 g, equal to the theoretical yield, were obtained.

The raw product, thus obtained was then treated with 1,500 ml of 2N sodium hydrate and completely solubilized by heating it under stirring. The product thus obtained was then added with charcoal, filtered, cooled to 0°–5° C. and kept at this temperature up to complete precipitation. The product was filtered, sucked on a filter, treated with 1,500 ml of 30% acetic acid and heated to 75°–80° C. This temperature was maintained for 1 hour, then the product was cooled at room temperature, filtered and then ground in demineralized water. The product thus obtained was then filtered and dried at a constant weight, thus obtaining 17–20 g of the product corresponding to a yield of 30–35%.

The compound was evaluated by thin layer chromatography according to the method described in Example 1 and showed an Rf equal to 0.6.

The compound was titrated by dissolving 0.15 g in 1 ml of ethylenediamine and 30 ml of DMF and titrating with isopropanolic KOH. The titration curve shows two acid groups and the molecular weight calculated by the alkali consumption resulted 285.

The NMR spectra in $D_2O + NaOD$ and in ethylenediamine show 3 triazolic CH groups. The IR spectrum shows the absorption bands of triazole and triazine rings. The elementary analysis gives the following results:

C=34.15%
N=63.15%

H=2.46%.
All data indicate a structure like

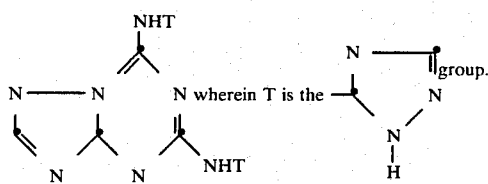

EXAMPLE 3

Preparation of Compound no. 3

Preparation of N,N'-bis-(1,2,4-triazolyl)-thiourea

A 3,000 ml multinecked flask provided with a reflux condenser and placed on a water bath was filled with 156.2 g (0.8964 mole) of N-1,2,4-triazolyl-dithiocarbamic acid methyl ester, prepared as described in U.S. Pat. No. 3,686,201, 1,700 ml of dimethylformamide, 75.37 g (0.8964 mole) of 3-amino-1,2,4-triazole. The reaction mixture was heated for 24 hours thus obtaining first a solution and then the formation of a precipitate. The suspension was filtered, the product thus obtained washed with methanol and then dried thus obtaining 109.3 g of a white product (Yield 57%).

| Percent analysis: | Calculated | Found |
| --- | --- | --- |
| | C = 28.57% | 28.59% |
| | H = 2.88% | 2.92% |
| | N = 53.31% | 53.24% |
| | S = 15.25% | 14.99% |

Preparation of N,N'-bis-(1,2,4-triazolyl)-s-methyl-isothiourea

A 1 liter multinecked flask provided with a stirrer, a reflux condenser, thermometer and a dropping funnel was filled with 400 ml of ethanol toluolate, 10.61 g of KOH. Stirring was continued to complete solution and the reaction mixture was added with 34.5 g (0.1641 mole) of N,N'-1,2,4-triazolyl-thiourea thus obtaining a suspension. 24 g (0.1670 mole) of methyl iodide were dropped thereon by maintaining the temperature at 25° C. Stirring was continued overnight, the reaction mixture was then filtered by washing it with alcohol. 32.7 g of a raw product were obtained. The raw product was finally crystallized from methanol thus obtaining 14.9 g of the desired product (Yield 40.48%).

| Percent analysis: | Calculated | Found |
| --- | --- | --- |
| | C = 32.14% | 31.80 |
| | H = 3.60% | 3.71% |
| | N = 49.97 | 48.18% |
| | S = 14.3% | 13.68% |

Preparation of N-(1,2,4-triazolyl)-s-methyl-isothiourea

A 6,000 ml multinecked flask provided with a stirrer, reflux condenser and dropping funnel with filled with 3,200 ml of methanol, 85 g (0.5937 mole) of N-(1,2,4-triazolyl)-thiourea, prepared according to the method described by G. Barnikow and J. Bödeker in J. pr., 313, 1148–1154 (1971). 84.2 g (0.5937 mole) of methyl iodide were dropped into the suspension which was then refluxed and boiled for two hours. The solution thus obtained was evaporated under vacuum till dry and the residue was dissolved in 1,000 ml of water. The solution was added with 10% sodium bicarbonate up to a pH equal to 7. A white product precipitated and this product was then filtered, washed with water and dried in a stove under vacuum at 50° C. 76.7 g of the desired product were obtained (Yield 82.47%).

| Percent analysis: | Calculated | Found |
| --- | --- | --- |
| | C = 30.56% | 30.30% |
| | H = 4.49% | 4.59% |
| | N = 44.56% | 44.29% |

Preparation of 3-guanidino-1,2,4-triazole

A 100 ml flask provided with bubblers was filled with 5 g (0.031847 mole) of N-(1,2,4-triazolyl)-s-methylisothiourea and absolute ethanol. Ammonia gas was bubbled therein up to saturation thus obtaining a complete solution. The obtained solution was poured into a closed tube, then heated to 120° C. for 16 hours and cooled. The solution was then evaporated to dryness under vacuum thus obtaining 3.6 g of the desired residue (Yield 80.64).

| Percent analysis: | Calculated | Found |
| --- | --- | --- |
| | C = 28.57% | 29.14% |
| | H = 4.80% | 4.84% |
| | N = 66.64% | 65.71% |

Preparation of 5,7-bis-(1,2,4-triazolyl-amino)-1,2,4-triazole-|1,5-a|-1,3,5-triazine (Compound no. 3)

A 15 ml one-necked flask was filled with 0.56 g (0.002497 mole) of N-(1,2,4-triazole)-s-methyl-isothiourea, 5 ml of dimethylformamide and 0.35 g (0.002775 mole) of 3-guanidino-1,2,4-triazole. A solution was obtained and this solution was then heated at 120° C. for 72 hours thus obtained a precipitate which was separated by filtration and washed first with dimethylformamide and then with acetone. The product thus obtained was dried under vacuum at 60° C. thus obtaining 0.35 g of the desired product (Yield 49.15%).

| Percent analysis: | Calculated | Found |
| --- | --- | --- |
| | C = 33.69% | 34.71% |
| | H = 2.47% | 2.17% |
| | N = 63.84% | 63.69% |

Mass, IR and NMR spectra and thin layer chromatography resulted similar to those of Compound of Example 2.

EXAMPLE 4

Preparation of Compound no. 4:
N,N'-bis-1,2,4-triazolyl-melamine

A 100 ml multi-necked flask provided with a reflux condenser, stirrer and dipped into an oil bath at 183° C. was filled with 20 ml of 2-phenylbutane, 12.6 g (0.15 mole) of 3-amino-1,2,4-triazone (prepared as described in U.S. Pat. No. 2,875,209) and 16.5 g (0.01 mole) of 6-amino-2,4-dichloro-1,3,5-triazine (prepared as described in B. 32, 695 (1899), O. Diels). The reaction mixture was heated to 183° C. and then cooled. The liquid was removed by decantation, the remaining solid was washed with 100 ml of acetone, ground in a mortar, suspended in 100 ml of boiling water, filtered and washed again with acetone. The white powder, thus obtained, was suspended in 20 ml of hot ethylenediamine at 80° C. and then filtered. The residue was washed with acetone and dried at 60° C. under vacuum, thus obtaining 1.9 g of a white solid.

| Percent analysis: | Calculated | Found |
|---|---|---|
| | C = 30.22% | 30.60% |
| | H = 3.62% | 3.83% |
| | N = 60.41% | 59.50% |

Mass spectrum: molecular ion at m/e=260

EXAMPLE 5

Preparation of Compound no. 5:
N,N',N''-tris-1,2,4-triazolyl-melamine

A 250 ml multinecked flask provided with a reflux condenser, stirrer and dipped into an oil bath at 183° C. was filled with 60 ml of 2-phenylbutane, 33.62 g (0.4 mole) of 3-amino-1,2,4-triazole and 3.68 g (0.02 mole) of 2,4,6-trichloro-1,3,5-triazino. The mixture was heated at 183° C. for 18 hours and then cooled. The liquid was removed by decantation, the solid residue was washed with 200 ml of acetone, ground in a mortar, suspended in 200 ml of boiling water twice, filtered and washed again with acetone. The obtained product was added with 100 ml of 10% NaOH under stirring. A complete solution was not obtained and the unsolved product was separated by filtration. The solution was then added with hydrochloric acid, thus obtaining a precipitate which was filtered and washed with water. The obtained product was dried at 60° C. under vacuum, thus obtaining 5 g of the desired product. (Yield 76.45%).

| Percent analysis: | Calculated | Found |
|---|---|---|
| | C = 31.3% | 32.03% |
| | H = 3.21% | 3.49% |
| | N = 60.85% | 61.06% |

EXAMPLE 6

Preparation of Compound no. 6:
5-amino-7-(1,2,4-triazolylamino)-1,2,4-triazole-|1,5-a|-1,3,5-triazine A 15 ml flask provided with a cooler was filled with 1.2 g of N-(1,2,4-triazolyl)-5-methyl-isothiourea (prepared as described in Example 3, and 5 ml of dimethylformamide. The reaction mixture was heated at 120° C. for 24 hours thus obtaining a precipitate which was the filtered. The residue was suspended in 100 ml of boiling water and boiling ethanol. 0.4 g of the desired product were obtained (Yield 48%).

| Percent analysis: | Calculated | Found |
|---|---|---|
| | C = 33.030% | 33.34% |
| | H = 2.77% | 2.70% |
| | N = 64.197 | 63.48% |

EXAMPLE 7

Preparation of Compound no. 7:
2,4-bis-(1,2,4-triazolylamino)-quinazoline

The reaction was performed as described for Compound no. 5 using 2,4-dichloro-quinazoline (prepared as described in J. Org. Chem., 27, 957–961 (1962), H. C. Scarborough, B. C. Lawes, J. L. Minielli, J. L. Compton) instead of 2,4,6-trichloro-1,3,5-triazine. 2.5 g of the desired compound were obtained. At NMR and IR analysis it resulted to correspond to the structure formula of Compound no. 7 having at mass spectrum a molecular ion at m/e=294.

EXAMPLE 8

Preparation of Compound no. 8:
2,4-bis-(1,2,4-triazolylamino)-6-methyl-pyrimidine hydrochloride The preparation was made as described for Compound no. 5 using 2,4-dichloro-3-methyl-pyrimidine instead of 2,4,6-trichloro-1,3,5-triazine, thus obtaining 21 g of the compound which at IR and NMR spectra resulted to correspond to the structure formula of Compound no. 8.

EXAMPLE 9

Preparation of Compound no. 9:
2,4,6-tris-(1,2,4-triazolylamino)-pyrimidine hydrochloride This compound was prepared as described for Compound no. 4 using 2,4,6-trichloro-pyrimidine instead of 2,4,6-trichloro-1,3,5-triazine thus obtaining 2.8 g of the compound which at IR analysis resulted to correspond to the structure formula of Compound no. 9.

| Percent analysis: | Calculated | Found |
|---|---|---|
| | C = 33.11% | 32.99% |
| | H = 3.05% | 3.17% |
| | N = 54.058% | 53.28% |

EXAMPLE 10

Preparation of Compound no. 10:
4,6-bis-(1,2,4-triazolylamino)-pyrazolo-|3,4-d|-pyrimidine This compound was prepared according to the method described for Compound no. 5 using 4,6-dichloro-pyrazolo-|3,4-d|-pyrimidine.

| Percent analysis: | Calculated | Found |
|---|---|---|
| | C = 35.76% | 33.80% |
| | H = 3.33% | 2.98% |
| | N = 55.61% | 55.63% |

EXAMPLE 11

Preparation of Compound no. 11:
5,7-bis-(1,2,4-triazolylamino)-1,2,4-triazolo-|2,3-a|-pyrimidine This compound was prepared according to the method described for Compound no. 5 using 5,7-dichloro-s-triazolo-|2,3-a|-pyrimidine prepared as described by Yasuo Makisumi in Chem. Pharm. Bull., 9, 801–8, Tokyo (1961).

| Percent analysis: | Calculated | Found |
|---|---|---|
| | C = 35.76% | 36.22% |
| | H = 3.33% | 3.18% |
| | N = 55.6% | 56.35% |

EXAMPLE 12

Preparation of Compound no. 12:
N,N',N''-tris-(5-methyl-1,2,4-triazolyl)-melamine hydrochloride This compound was prepared according to the method described for Compound no. 2 using 3-amino-5-methyl-1,2,4-triazole (prepared as described in G.B. Pat. No. 765,728) instead of 3-amino-1,2,4-triazole.

| Percent analysis: | Calculated | Found |
|---|---|---|
| | C = 32.558% | 32.22% |
| | H = 3.874% | 3.98% |
| | N = 47.50% | 46.4% |

EXAMPLE 13

An emulsion having mainly internal sensitivity has been prepared by adding in 10 minutes 0.56 mole of silver chloride precipitated in the presence of gelatin to a water gelatin solution containing 0.84 mole of potassium bromide and 0.012 mole of potassium iodide and heating 20 minutes at 70° C. to convert the silver chloride emulsion in a silver bromo-chloro-iodide emulsion.

The emulsion was flocculated by adding sodium sulfate, washed and reconstituted in such a way to have a final content of 0.3 mole silver halide per each Kg of gelatin and a silver to gelatin ratio of 0.8. In all steps inert ossein gelatin was used.

When such emulsion was coated (on a triacetate support base), step-wedge exposed for 10 seconds under an illumination of 6500 lux of a tungsten lamp and developed for 6 minutes at 20° C. in Developers A and B, the results of Table 1 were obtained (in the following tables, the maximum density and minimum density values are respectively indicated as $D_M$ and $D_m$).

TABLE 1

| Developer A | | Developer B | |
|---|---|---|---|
| Step no. | $D_M$ | Step no. | $D_M$ |
| 0 | 0.04 | 13 | 0.90 |

(*) Each step corresponds to 0.3 logE.

No image was visible with surface developer A and a negative image was obtained with Developer B. This emulsion satisfies the conditions for an internal image emulsion.

The emulsion described above was coated after having added for each mole of silver halide:
(a) 700 ml of a 6% dispersion of yellow Coupler A and 0.3% of 2,5-ditert.-butyl-hydroquinone in dibutylphthalate and tricresylphosphate
(b) 128 ml of a solution containing 0.1 g of Compound no. 1 in 100 ml of 0.1N NaOH, and
(c) 128 ml of 0.1N $H_2SO_4$.

The silver coating weight was 1.5 g Ag/m². A gelatin top coating containing a hardener was added to improve the mechanical properties of the film.

Samples of this film (Coating I) were exposed as described above and processed for 6 minutes at 20° C. in A and others for 3.5 minutes at 36° C. in color developer C. After development, the strips processed in A were fixed, while those processed in C were bleached and fixed.

The strip processed in A did not show any image; the strip processed in C showed a positive image, the properties of which are reported in Table 2.

TABLE 2

| | Developer A | | Developer C | | |
|---|---|---|---|---|---|
| Coating | Step no. | Fog | Step no. | $D_M$ | $D_m$ |
| I | 0 | 0.04 | 12 pos. | 0.80 | 0.05 |

EXAMPLE 14

Five coatings as those described in Example 13 were prepared replacing yellow Coupler A with the following couplers (Cp): B (magenta); C (magenta); D (cyan); E (cyan); F (cyan).

The strips were exposed and processed as described in Example 13. All strips processed in Developer A showed no image or a very weak negative image, while when processed in Developer C all showed a magenta or cyan positive image as illustrated in Table 3.

TABLE 3

| | | Developer A | | Developer C | | |
|---|---|---|---|---|---|---|
| Coat. | Coup. | Step no. | $D_M$ | Step no. | $D_M$ | $D_m$ |
| II | B | 0 | 0.03 | 13 Pos. | 1.20 | 0.03 |
| III | C | 0 | 0.03 | 12 Pos. | 0.52 | 0.06 |
| IV | D | 0 | 0.03 | 12 Pos. | 0.53 | 0.03 |
| V | E | 8 Neg. | 0.09 | 13 Pos. | 0.72 | 0.08 |
| VI | F | 8 Neg. | 0.03 | 12 Pos. | 0.40 | 0.16 |

The experiments described in Examples 13 and 14 show that the positive image was obtained independently from the nature of the coupler and that by chosing the right coupler it is possible to obtain a yellow, magenta and cyan positive image as required to make a color picture.

EXAMPLE 15

The emulsion C described by G. C. Farnell, R. L. Jenkins and L. R. Solman in J. Phot. Sci., 24, 1 (1976) was prepared by using inert gelatin. This emulsion was coated, exposed and processed as described for the emulsion of Example 13. The results obtained are reported in Table 4.

TABLE 4

| Developer A | | Developer B | |
|---|---|---|---|
| Step no. | $D_M$ | Step no. | $D_M$ |
| 15 | 0.18 | 16 | 0.90 |

These results show that the emulsion has mainly an internal sensitivity.

Three coatings VII, VIII and IX were made with such emulsion as described in Example 13 using Coupler A (yellow), B (magenta) and E (cyan), respectively.

The strips were then exposed and processed as described in Example 13. All strips processed in A showed a weak negative image while those processed in the color developer showed a good positive image as reported in Table 5.

Table 5

| Coat. | Coup. | Developer A | | Developer C | | |
|---|---|---|---|---|---|---|
| | | Step no. | $D_M$ | Step no. | $D_M$ | $D_m$ |
| VII | A | 10 Neg. | 0.10 | 14 Pos. | 0.76 | 0.03 |
| VIII | B | 10 Neg. | 0.12 | 14 Pos. | 0.80 | 0.10 |
| IX | E | 10 Neg. | 0.10 | 14 Pos. | 1.50 | 0.06 |

This experiment shows that the claimed effect is not limited to a particular emulsion formulation, but it is valid on at least two different formulations of internal sensitivity emulsions.

EXAMPLE 16

The emulsion described in Example 15, sensitized respectively to the green and red regions of the spectrum, was used to prepare the following coating compositions X and XI:

(X) 140 mg of a green (spectral) sensitizer, 700 ml of a 6% dispersion of magenta coupler B and 0.3% of 2,5-ditert.-butyl-hydroquinone in dibutylphthalate and tricresylphosphate, 128 ml of a solution containing 0.1 g of Compound 1 in 100 ml of 0.1N NaOH and 128 ml of 0.1N $H_2SO_4$;

(XI) 230 mg of a red (spectral) sensitizer, 700 ml of a 6% dispersion of cyan coupler E and 0.3% di 2,5-ditert.-butyl-hydroquinone in dibutylphthalate and tricresylphosphate, 128 ml of a solution containing 0.1 g of Compound 1 in 100 ml of 0.1N NaOH and 128 ml of 0.1N $H_2SO_4$.

The coating weight on the triacetate support base for both coatings was 1.5 g $Ag/m^2$. A top gelatin coating containing a hardener was added to improve the mechanical properties of the film.

Strips of coatings X and XI together with coating VII of Example 15 were exposed for 10 seconds under an illumination of 6500 lux from a tungsten lamp through the blue, green and red filters normally employed for the evaluation of color separation and developed in C as described in Example 13. Three positive images, yellow, magenta and cyan, were obtained with the properties reported in Table 6.

TABLE 6

| Coat. | Coup. | No. of positive steps through the filters | | | $D_M$ |
|---|---|---|---|---|---|
| | | Blue | Green | Red | |
| VII | A | 10 | 0 | 0 | 0.90 |
| X | B | 11 | 15 | 0 | 1.30 |
| XI | E | 12 | 13 | 15 | 1.50 |

The experiment shows that color separation suitable to make a color film can be obtained.

EXAMPLE 17

Coating VII of Example 15 was compared with a similar coating in which Compound no. 1 had been added to the coating composition of the protective layer instead of the emulsion layer, in the amount of 12 mg of Compound 1 for each 10 g of gelatin.

The two strips, exposed and developed in C for 3 minutes and a half at 36° C., gave yellow positive images having substantially the same speed, maximum and minimum densities.

This experiment indicates that the D.A.P. agent 1 may be present in an adjacent layer and still gives the same photographic effect.

EXAMPLE 18

The emulsion described in Example 15 was used to compare Compound no. 4 with Compound no. 1. This emulsion was added with 540 ml for each silver mole of a 6% dispersion of yellow coupler A as described in Example 13, then divided into 7 parts and added with Compounds no. 1 and 4 according to the amount indicated in the second column of Table 7. Both Compounds no. 1 and 4 had dissolved in 0.1N at the concentration of 0.1% before being added to the emulsion. Each part was coated at a pH of 6.5 and a silver coating weight of 1.5 $Ag/m^2$. A gelatin top coating containing a hardener was then coated onto each coating to improve the mechanical properties of the film.

Each coating was step-wedge exposed for 10 seconds under an illumination of 6,500 lux from a tungsten lamp and developed for 3 minutes and a half in color developer C and then bleached and fixed.

All strips showed a positive image. The properties are reported in Table 7.

TABLE 7

| Coating | Comp. no. | Amount mg/M Ag | Step no. | $D_M$ | $D_m$ |
|---|---|---|---|---|---|
| XII | 1 | 36 | 12.5 | 1.12 | 0.06 |
| XIII | 1 | 9 | 13 | 1.00 | 0.06 |
| XIV | 4 | 36 | 13 | 1.17 | 0.06 |
| XV | 4 | 18 | 13.5 | 1.20 | 0.06 |
| XVI | 4 | 9 | 13.5 | 0.96 | 0.06 |
| XVII | 4 | 4.5 | 14 | 0.90 | 0.06 |
| XVIII | 4 | 2.25 | 14 | 0.78 | 0.06 |

Compound no. 4 allowed to achieve higher speed than Compound no. 1 and moreover lower amount was needed to reach the best effect. This conclusion was confirmed by coating magenta (Coupler B) and cyan (Coupler E) layers (coatings XIX to XXVI) analogous to those described in Example 16. The results are reported in Table 8.

TABLE 8

| Coating | Comp. no. | Amount mg/M Ag | Layer | Step no. | $D_M$ | $D_m$ |
|---|---|---|---|---|---|---|
| XIX | 1 | 36 | cyan | 14 | 1.85 | 0.06 |
| XX | 4 | 36 | cyan | 15 | 1.90 | 0.06 |
| XXI | 4 | 18 | cyan | 15 | 2.00 | 0.06 |
| XXII | 4 | 9 | cyan | 15 | 1.75 | 0.06 |
| XXIII | 1 | 36 | magenta | 13.5 | 1.86 | 0.06 |
| XXIV | 4 | 36 | magenta | 14.5 | 1.60 | 0.06 |
| XXV | 4 | 18 | magenta | 14.5 | 1.56 | 0.06 |
| XXVI | 4 | 9 | magenta | 14.5 | 1.00 | 0.06 |

EXAMPLE 19

Three coatings XXVII, XXVIII and XXIX were made with the emulsion described in Example 15. Coating XXVII contained 550 ml for each mole of silver halide of a 6% dispersion of yellow Coupler A as described in Example 13; coating XXVIII contained 550 ml for each mole of silver halide of a 6% dispersion of magenta Coupler B as described in Example 16; coating XXIX contained 550 ml for each mole of silver halide of a 6% dispersion of cyan Coupler E as described in Example 16. The silver coating weight was 1.5 g $Ag/m^2$. A gelatin top coating containing a hardener was added to improve the mechanical properties of the film.

Strips of the three films were step-wedge exposed for 10 seconds under an illumination of 6500 lux from a TABLE 12-continued

| Coating | Step no. | $D_M$ | $D_m$ |
|---|---|---|---|
| XL | 16 | 2.20 | 0.02 |

EXAMPLE 24

The emulsion of Example 13 was added with a complex and 9.3 μM of compound 3 per Mole of silver formed on polyethylacrylate as described in Example 26 and then divided into three parts (A, B and C) and the following additions were made:
  (A) No further addition
  (B) 25.7 g of red pigment Colanil Red per each mole of silver
  (C) 33 g of yellow pigment Colanil Yellow for each mole of silver The parts A, B and C were respectively coated on a resin-coated paper with a silver coating weight of 1 g/m² to give coatings XLI, XLII and XLIII.

The material was then step-wedge exposed for 10 seconds under an illumination of 6,500 lux from a tungsten lamp and processed for 30 seconds at 30° C. in the tanning developer obtained by mixing the following solutions A and B just before use:
(A)
  Water: 700 ml
  Na₂SO₄: 120 g
  Hydroquinone: 5 g
(B)
  Water: 300 ml
  Na₂CO₂: 10 g The results are reported in the following Table 13.

TABLE 13

| Coating | Step no. | $D_M1$* | $D_M2$** | $D_m1$* | $D_m2$** |
|---|---|---|---|---|---|
| XLI | 12 P | 0.34 | | 0 | |
| XLII | 11 P | 0.95 | 1.7 | 0 | 0 |
| XLIII | 10 P | 0.40 | 1.15 | 0 | 0 |

1* = Lectures with white light
2** = Green light for coating XLII and blue light for coating XLIII.

We claim:

1. An internal latent image silver halide photographic emulsion having in contact therewith developer autoxidation promoter agents comprising compounds having at least one 1,2,4-triazolyl-5-amino-azomethine group, the carbon atom and the nitrogen atom of said azomethine being a part of a nitrogen-containing heterocyclic nucleus.

2. An internal latent image silver halide photographic emulsion having in contact therewith developer autoxidation promoter agents comprising compounds having at least one 1,2,4-triazolyl-5-amino-azomethine group, the carbon atom and the nitrogen atom of said azomethine being a part of a nitrogen-containing heterocyclic nucleus, and all other heterocyclic nuclei in said compound being comprised of only nitrogen and carbon atoms having five or six ring atoms and no more than three nitrogen atoms within each ring.

3. The internal latent image silver halide photographic emulsion of claim 1 wherein said heterocyclic nucleus is selected within the group including triazine, pyrimidine, pyridazine, benzopyrimidine and triazolotriazine.

4. The internal latent image silver halide photographic emulsion of claim 1 wherein said chemical compound is represented by the general formula:

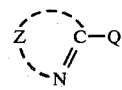

wherein Q represents —NR₁R₂ and R₁ and R₂ each represent hydrogen or a 5-(1,2,4)-triazolyl group, at least one of them being different from hydrogen, and Z represents the non-metallic atoms necessary to form a 5 or 6 membered heterocyclic nucleus.

5. The internal latent image silver halide photographic emulsion of claim 1 wherein said chemical compound is represented by the general formula:

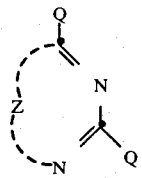

wherein Q represents —NR₁R₂ and R₁ and R₂ each represent hydrogen or a 5-(1,2,4)-triazolyl group, at least one of them being different from hydrogen, and Z represents the non-metallic atoms necessary to form a 5 or 6 membered heterocyclic nucleus.

6. An internal latent image silver halide photographic emulsion having in contact therewith, as developer autoxidation promoter agent, a complex of divalent copper with the chemical compounds of claim 1.

7. The internal latent image silver halide photographic emulsion of claim 1 wherein the developer autoxidation promoter agent is associated therewith in the presence of a dispersed carrier compound.

8. The internal latent image silver halide photographic emulsion according to claim 6 wherein the carrier compound is selected from the group of a polyethylacrylate, a polyurethane, silica and starch compounds.

9. The photographic emulsion according to claim 2 wherein the developer autoxidation promoter agent is present in an amount of 0.0001 to 0.1 gram per mole of silver.

10. The photographic emulsion according to claim 3, optically sensitized to a region of the visible spectrum and associated to image dye providing compounds wherein the developer autoxidation promoter agent is associated with a thiobarbituric acid compound.

11. The internal latent image silver halide photographic emulsion according to claim 9, wherein the image-dye providing compounds are associated with diffusion-resistant hydroquinones.

12. A direct positive photographic element comprising at least one gelatin light sensitive silver halide emulsion layer which contains the silver halide emulsion of claim 1.

13. A multilayer direct positive color photographic element comprising at least three gelatin silver halide emulsion layers respectively sensitive to the red, to the green and to the blue region of the visible light and associated with image-dye providing compounds charcterized by the fact that at least one of said emulsion layers includes the silver halide emulsion of claim 1.

14. The multilayer direct positive color photographic element according to claim 12 wherein the red-sensitungsten lamp and developed for 3 minutes and a half at 36° C. in color developer C in which different amounts of the sodium salt of the Compound 2 had been dissolved in the amount indicated in Table 9.

In absence of the compound of Example 2, or when this was present in an unsufficient amount, no image was obtained.

TABLE 9

| Coating | Quantity (mg) of Compound 2 | | | | | | | | | | |
|---|---|---|---|---|---|---|---|---|---|---|---|
| | 0 | 0.001 | 0.01 | | | 0.02 | | | 0.1 | | |
| | S | S | S | $D_M$ | $D_m$ | S | $D_M$ | $D_m$ | S | $D_M$ | $D_m$ |
| XXVII | 0 | 0 | 15.5 | 0.16 | 0.06 | 15.5 | 0.65 | 0.06 | 15.5 | 1.04 | 0.06 |
| XXVIII | 0 | 0 | 15.5 | 0.36 | 0.04 | 15.5 | 1.10 | 0.04 | 15.5 | 1.26 | 0.04 |
| XXIX | 0 | 0 | 15.5 | 0.95 | 0.04 | 15.5 | 1.50 | 0.04 | 15.5 | 2.00 | 0.04 |

S = Step number. Each step is 0.3 logE
S = 0 indicates the presence of background fog alone.

EXAMPLE 20

A single layer was coated with the emulsion used in Example 19. Such layer for each mole of silver halide contained 210 ml of the yellow Coupler A dispersion, 175 ml of the magenta coupler B dispersion and 140 ml of the cyan coupler E dispersion. The material was hardened and exposed as described hereinbefore and then developed for 3 minutes and a half at 36° C. in C which contained 0.1 mg of Compound 2 and not bleached as usual but only fixed.

A positive black and white image was obtained having 15.5 steps, a minimum density of 0.04 and a maximum density, measured through blue, green and red filters, of 0.64, 0.68 and 0.68, respectively.

EXAMPLE 21

Coating compositions were prepared similar to those of coatings VII, X and XI of Example 16. Each composition was divided into two portions and one of these was added with $85 \times 10^{-6}$ mole of thiobarbituric acid for each mole of silver halide. The six compositions were then coated (coatings XXX to XXXV), exposed and processed as described in Example 13, thus obtaining six positive yellow, magenta and cyan images having the properties described in the following Table 10.

This experiment indicates that the addition of thiobarbituric acid increases the maximumdensity.

TABLE 10

| Coating | Thio-barbituric acid | No. Positive Steps through the filters | | | $D_M$ | $D_m$ |
|---|---|---|---|---|---|---|
| | | Blue | Green | Red | | |
| XXX | no | 10 | 0 | 0 | 0.90 | 0.05 |
| XXI | yes | 10 | 0 | 0 | 1.20 | 0.05 |
| XXXII | no | 11 | 15 | 0 | 1.20 | 0.06 |
| XXXIII | yes | 11 | 15 | 0 | 1.60 | 0.06 |
| XXXIV | no | 12 | 13 | 15 | 1.55 | 0.05 |
| XXXV | yes | 12 | 13 | 15 | 2.00 | 0.05 |

EXAMPLE 22

A cyan layer composition was prepared with a red-sensitized silver chloro-bromo-iodide emulsion similar to that of Example 13 containing 2.4% silver iodide and comprising, per 1 Kg of emulsion, 50 g of gelatin, 10 ml of 0.05% thiobarbituric acid and 900 g of a 6% dispersion of Coupler E as described in Example 16.

This composition was divided into 3 parts A, B and C. Part A was added with 44 μM/M silver of $CuCl_2$, followed by 7 μM/M silver of Compound no. 3. Parts B and C were added with 128 ml of a 20% polyethylacry-late dispersion wherein the compound no. 3—Cu complex had been formed by adding a 0.01% $CuCl_2.2H_2O$ and a 0.01% Compound 3 solution. Part B contained 44 μM/mole of silver of $CuCl_2$ and 7 μM/mole of silver of Compound no. 3, as Part A. Part C contained 44 μM/Ag M of $CuCl_3$ and 3.5 μM/Ag M of Compound no. 3.

Parts A, B and C were coated on a resin-coated paper at a silver coating weight of 1 g/m² with a top layer having the composition described in Example 25 to give respectively Coatings XXXVI, XXXVII and XXXVIII.

The coatings were step-wedge exposed for 10 seconds under an illumination of 6,500 lux and processed in Developer D. The results are reported in Table 11.

TABLE 11

| Coating | Steps no. | $D_M$ | $D_m$ |
|---|---|---|---|
| XXXVI | 16.5 | 1.80 | 0.02 |
| XXXVII | 15.5 | 3.20 | 0.02 |
| XXXVIII | 16.5 | 1.63 | 0.02 |

The same results were obtained by forming the complex on a 20% dispersion of a polyurethane latex or a 20% Ludox HS (TM) dispersion.

EXAMPLE 23

The composition described in Example 22 was coated on a polyester base at a coverage of 1 g/m² of silver. A top coating comprising the Cu complex of Compound 3 was then coated on the emulsion layer according to the following procedure:

(1) one part of the emulsion layer (coating XXXIX) was coated with a top layer composition consisting of 85 ml of the following solution for each 10 g of gelatin:
Ludox HS (TM) 20%: 250 ml,
$CuCl_2.2H_2O$ 0.01%: 550 ml,
Compound 3 0.01% in 0.01M KOH: 50 ml, (2) a second part of the emulsion layer (coating XL) was coated with a top layer composition comprising 8 ml of the following solution for each 10 g of gelatin:
$CuCl_2.2H_2O$ 0.05%: 250 ml,
Soluble starch: 1 g,
Compound 3 0.01% in 0.02M KOH: 92.5 ml,
(prepared by dissolving starch in $CuCl_2$ boiling solution cooling and adding the compound 3 solution).

The two coatings, exposed and processed as described in Example 26, gave the results reported in Table 12.

TABLE 12

| Coating | Step no. | $D_M$ | $D_m$ |
|---|---|---|---|
| XXXIX | 15 | 2.20 | 0.02 | tive, the green-sensitive and the blue-sensitive silver halide emulsion layers respectively comprise incorporated therein cyan-dye, magenta-dye and yellow-dye forming couplers.

15. A direct positive photographic element including a light-sensitive silver halide emulsion layer associated with a colored pigment and a tanning developer, characterized by the fact that said silver halide emulsion is the emulsion of claim 1.

16. A process for forming a direct positive image by developing, after image-wise exposure, an internal latent image type light-sensitive silver halide photographic element with a low sulfite containing silver halide developer, which process is characterized by contacting said silver halide emulsion with the developer autoxidation promoter agents of claim 1.

17. A process for forming multicolor direct positive images by developing, after image-wise exposure, a multilayer photographic element comprising internal latent image type silver halide emulsion layers, respectively sensitive to the red, to the green and to the blue region of the visible light and associated with image-dye providing compounds, with a p-phenylene diamine color developer composition, which comprises contacting said silver halide emulsions with the developer autoxidation promoter agents of claim 1.

18. A process for forming a direct positive colored relief image by developing, after image-wise exposure, an unhardened gelatin internal latent image type silver halide emulsion photographic element associated with a colored pigment and a tanning developer, with an aqueous alkaline solution, which process is characterized by contacting said silver halide emulsion with the developer autoxidation promoter agents of claim 1.

* * * * *